United States Patent [19]
Saitoh

[11] Patent Number: 5,980,742
[45] Date of Patent: Nov. 9, 1999

[54] DEGASSING UNIT FOR HIGH PERFORMANCE LIQUID CHROMATOGRAPHY

[75] Inventor: Toshinori Saitoh, Akishima, Japan

[73] Assignee: Micro Electronics, Inc., Tokyo, Japan

[21] Appl. No.: 09/186,870

[22] Filed: Nov. 4, 1998

[51] Int. Cl.⁶ .................................................. B01D 15/08
[52] U.S. Cl. ...................... 210/198.2; 210/656; 210/186; 95/46; 96/6
[58] Field of Search .................................. 210/656, 188, 210/198.2; 95/46; 96/219, 194, 6

[56] References Cited

U.S. PATENT DOCUMENTS

| | | | |
|---|---|---|---|
| 5,019,140 | 5/1991 | Bowser | 96/6 |
| 5,183,486 | 2/1993 | Gatten | 210/198.2 |
| 5,244,478 | 9/1993 | Jolly | 96/6 |
| 5,279,647 | 1/1994 | Gatten | 96/6 |
| 5,298,340 | 3/1994 | Gatten | 210/198.2 |
| 5,522,917 | 6/1996 | Honda | 96/6 |
| 5,693,122 | 12/1997 | Berndt | 96/6 |
| 5,711,882 | 1/1998 | Hofmann | 96/6 |
| 5,762,684 | 6/1998 | Hayashi | 96/6 |
| 5,788,742 | 8/1998 | Sugimoto | 96/6 |

*Primary Examiner*—Ernst G. Therkorn
*Attorney, Agent, or Firm*—Lackenbach Siegel Marzullo, Aronson & Greenspan, P.C.

[57] ABSTRACT

Used for high performance liquid chromatography systems, a degassing unit with degassing performance of high fluid replacement efficiency in a small volume is described, which is composed of (1) a flat rectangular hollow enclosure using two rectangular degassable film sheets which fringes are sealed hermetically to form an internal space, and providing two independent openings at separate positions; one for an inlet to feed eluent in and the other for an outlet to feed it out, (2) two sheet plates with a number of holes, of the same shape as that of the film sheets, each of which is closely fitted to either side of the film sheets to prevent the expansion of the hollow enclosure, (3) a degassing module having the fringe of the hollow enclosure and the fringes of the plates with holes piled in one upon another with a pair of holding frames which allow to expose the outside surface areas of the sheet plates, (4) a vacuum chamber accommodating the degassing module and enclosing the surrounding space around it, and (5) a vacuum pump which reduces a pressure in the surrounding space.

15 Claims, 12 Drawing Sheets

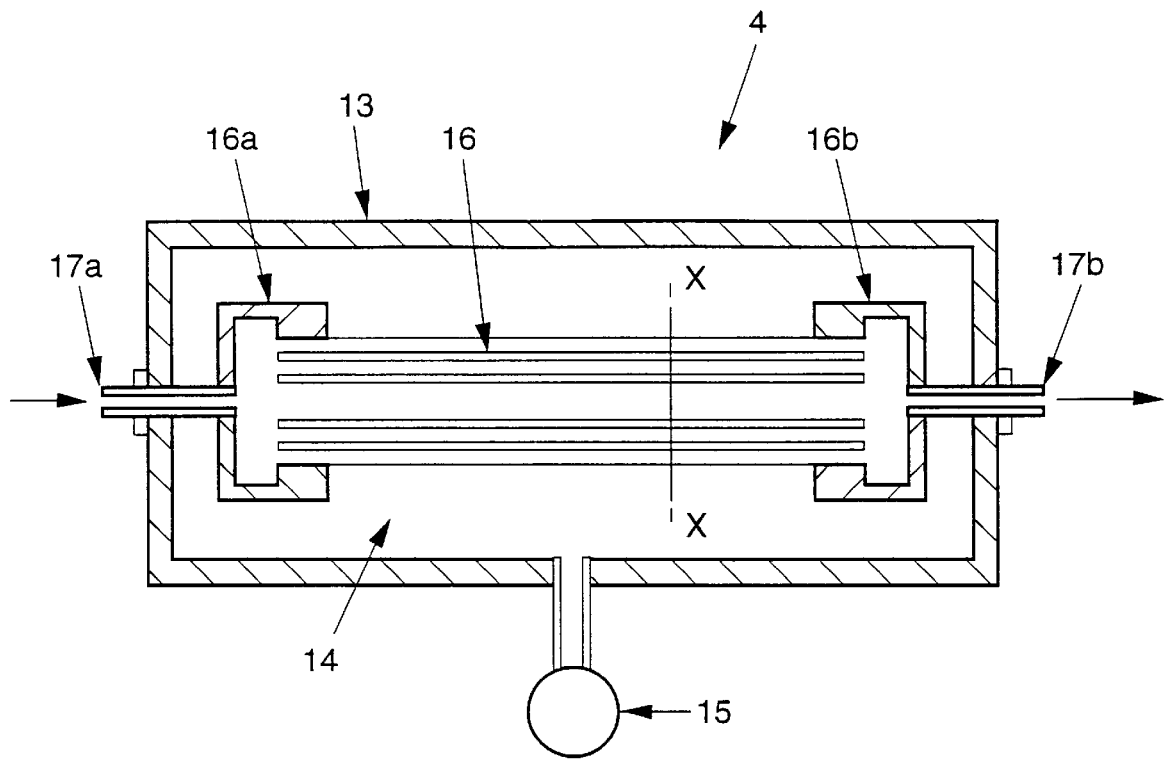
FIG. 11 (a) PRIOR ART
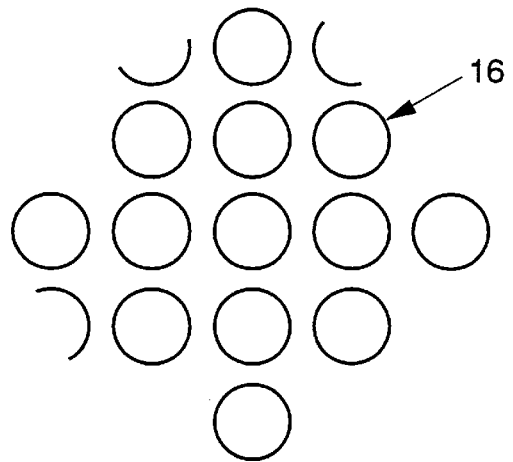
FIG. 11 (b) PRIOR ART

DEGASSING UNIT FOR HIGH PERFORMANCE LIQUID CHROMATOGRAPHY

BACKGROUND OF THE INVENTION

1. Technical Field

This invention relates to a degassing module which is used as a degassing unit for high performance liquid chromatography (hereinafter called HPLC) systems. It removes gaseous compounds dissolved in eluent which is separated and analyzed by the liquid chromatography, thereby allowing to make a fine and precise fluid delivery at a high speed required for HPLC.

2. Background Art

There is a tendency that HPLC used to separate compounds in a given sample is made more and more highly accurate. Usually in this type of HPLC, an eluent drawn from a reservoir by a fluid delivery pump is delivered via a sample injection valve to a detecting section including a separation column. In high speed and high accuracy liquid chromatography systems (known as semi-micro HPLC and micro HPLC) which requires high accuracy in delivering the eluent under a high pressure yet at a very small quantity, it is common to install a degassing unit on the inlet side of the fluid delivery pump in order to insure the stability of the pump.

The purpose to install this type of degassing unit is to remove unnecessary gases dissolved in the eluent. Especially when an electrode reduction reaction is measured, oxygen dissolved in the eluent greatly influence its measured value. That is, the reduction reaction of the oxygen themselves makes a big background current, thereby causing noises to be increased.

FIG. 10 is a block diagram to explain a system configuration of HPLC. An eluent 2 in a first reservoir 1 is drawn up by a pump 5 through a pipe 3 and degassed by a degassing unit 4. It is then delivered through a sample injection valve (auto sampler) 6 and 3 column 7 to a detector unit 8. The eluent delivered from the detector unit 8 is thrown out to a second reservoir 10 as a waste eluent 9. The arrow marks show the direction of the eluent delivery. Data detected by the detector unit 8 are transferred to a data processing unit 11, wherein they are processed in a visual form or a computer processable data form to provide and store. The column 7 is accommodated in an isothermal oven 7A to prevent the influence of external temperature. The pump 5 and the sample injection valve 6 are controlled by a system controller 12. The degassing unit 4 is installed before the pump 5 to insure the stable delivery of the fluid and the accurate analysis by removing gases dissolved in the eluent which is drawn up from the first reservoir 1 by the pump 5.

As it is well known about other units and components consisting of this kind of high accuracy liquid chromatography as well as about the function of the whole system, those explanations are omitted.

FIGS. 11(*a*) and (*b*) illustrate a compositional example of a conventional degassing unit, showing its overall cross sectional view in FIG. 11(*a*) and its principal part in cross section in FIG. 11(*b*), respectively.

As shown in FIG. 11(*a*), the conventional degassing unit is composed of a degassing module 14 accommodated inside a hermetically sealed room (vacuum chamber) 13 and a vacuum pump 15 to evacuate air from the chamber 13. The degassing module 14 consists of capillary tubes 16 made of such material inactive to corrosive liquid or gases in various organic solvents as Polytetra Fluoro Ethylene (PTFE), both of which ends are bundled by multi-connectors 16*a* and 16*b*. The multi-connector 16*a* is connected through a joint tube 17*a* to the outside of the chamber 13. The joint tube 17*a* is then connected to the first reservoir 1 via the pipe 3 as shown in FIG. 10. The multi-connector 16*b* is connected through a joint tube 17*b* to the outside of the chamber 13 as well, where it is then connected to the inlet of the pump 5 as shown in FIG. 10. A number of the capillary tubes 16 made of gas permeable resin like PTFE or others to compose the degassing module 14 are bundled as shown in the FIG. 11(*b*). The inside of the chamber 13 is reduced in pressure by the vacuum pump 15, thereby reducing the pressure in the space between the bundled capillary tubes. Consequently, gases dissolved in the eluent flowing inside the capillary tubes 16 are extracted to the inside of the chamber 13.

As mentioned above, the conventional degassing unit is composed of the degassing module 14 made with the capillary tubes of gas permeable resin such as silicon resin or PTFE which is inactive to the eluent yet good in gas permeability, the vacuum chamber 13, and the vacuum pump 15. By flowing the eluent in the capillary tunes 16 of PTFE or others for the degassing module 14, and by reducing the pressure outside the capillary tubes by the vacuum pump 15, the degassing unit is provided with the function to remove gaseous compounds dissolved in the eluent flowing inside the capillary tubes. The eluent is degassed by passing through the degassing unit, and sent out to the detection means by the fluid delivery pump, thereby making it possible to deliver the eluent stably and accurately to the detection means regardless of changes in ambient temperature.

Generally, an amount of gases dissolved in a liquid is not always constant. It is proportional to pressure, and the higher the pressure the more the amount of gases dissolved. This means the amount of gases dissolved is dependent on a change of the atmospheric pressure.

On the other hand, it is also dependent on temperature. If the pressure is constant, the lower the temperature the more the amount of gases dissolved. To put it concretely, as the temperature is lower in the morning than in the day time, the amount of gases dissolved in the eluent is large in the morning and becomes small in the day time. When starting delivering the fluid in the morning, gas bubbles tend to be observed in the capillary tubes connected to the fluid pump as the temperature goes up toward the day time. It shows that the amount of gases dissolved in the eluent is reduced by an increase of the surrounding temperature. The generation of gas bubbles due to the increase of the temperature becomes a worst condition for such a case that the eluent has to be cooled.

For example, when the room temperature fluctuates in a range of 25–30 degrees C., the temperature of the eluent that is cooled at 5 degrees fluctuates at 20–25 degrees C. and it is observed that gas bubbles are suddenly generated inside the capillary tubes.

In this connection, the degassing unit plays an important role to perform the stable fluid delivery of fine amount precisely regardless of changes of the surrounding conditions. For details on this type of high accuracy liquid chromatography, refer to U.S. Pat. No. 5,472,598.

A standard high performance liquid chromatography (HPLC) system being conventionally used is configured with its column sizes of 4.6 mm in diameter and 250 mm in length at a speed (pump flow speed) of 1–1.5 ml/min. in fluid delivery by a pump.

In addition to this, recently developed were semi-micro HPLC systems with a very small volume of column by making its size smaller which is 1.0–2.0 mm in diameter and 250 mm in length at a fluid delivery speed of 50–300 μl/min. Those were followed by micro HPLC systems by making its column size further smaller which is 0.5–1.0 mm in diameter and 250 mm in length at a fluid delivery speed of 10–50 μl/min. In order to configure such a micro HPLC system as mentioned above, it is required to make an attached degassing unit being of microstructure as well.

However, in attempting the degassing unit to be of microstructure problems arise in an internal volume and a structure of a degassing module as the functional part. The internal volume of a degassing module in a standard HPLC system has a capacity of 12 ml, which is too big to apply to the semi-micro and micro HPLC systems. That is, as the pump flow speed in semi-micro HPLC is 0.1–0.2 ml/min. as mentioned above, it takes 60–120 min. even in simple calculation for the fluid to pass through the degassing module. This is considerably long for the time of chromatographic analysis.

The capillary tubes of PTFE or others for the degassing module are commonly used in a bundle of 18 tubes with the length of 2,500 mm. The fluid is distributed into the respective capillary tubes to flow. However, as every tube is not the same in flow resistance, speeds for the fluid to pass through the tubes are different between them. Because of the difference in fluid speed, the time required for the fluid to be replaced completely inside the module is not 60–120 minutes as previously obtained in simple calculation, but it actually takes a few to several times more (325 minutes) as shown in Table 1.

Therefore, even if the volume of the tubes is made smaller in order to make the module internal volume small, it takes long to replace the fluid in the area of semi-micro HPLC if the structure of the degassing module is kept the same as it is.

Table 1 shows a relationship of fluid replacement volume and time by the conventional tube module in comparison with by flat film module of this invention which details are described hereunder.

TABLE 1

|  | Replacement volume | Replacement time (1 ml/min) | Replacement time (0.2 ml/min) |
| --- | --- | --- | --- |
| Tube module | 65 ml | 65 min. | 325 min. |
| Flat film module | 9.8 ml | 9.8 min. | 49 min. |

(Note) Internal volume of module
Tube module: 12 ml
Flat film module: 1.6 ml

In this connection, there was a problem that even if just applying the conventional degassing module to semi-micro HPLC it greatly increases the replacement time, making it unable to suitably comprise a semi-micro HPLC system of practical performance.

SUMMARY OF THE INVENTION

The purpose of this invention is to provide a degassing unit allowing to degas with a small volume yet high fluid replacement efficiency.

To achieve the above purpose, this invention is characterized by having the following composition.

(1) The invention is a degassing unit to be used for high performance liquid chromatography (HPLC) systems, which draws eluent from its reservoir by a fluid delivery pump, removes gases dissolved in the eluent, delivers the gas removed eluent via a sample injection valve to a detection means including a separation column, and is installed between the aforementioned reservoir and the fluid delivery pump. This degassing unit is provided with the following:

A flat rectangular hollow enclosure consisting of two rectangular degassable film sheets which fringes are sealed hermetically to form an internal space, and providing two independent openings at separate positions; one for an inlet to feed the eluent in and the other for an outlet to feed it out.

Two sheet plates wits a number of holes, of the same shape as that of the aforementioned film sheets, each of which is closely fitted to either side of the film sheets to prevent the expansion of the hollow enclosure.

A degassing module having the fringe of the hollow enclosure and the fringes of the sheet plates with holes piled in one upon another with a pair of holding frame, which allow to expose the outside surface areas of the sheet plates.

A vacuum chamber accommodating the degassing module and enclosing the surrounding space around it A vacuum pump which reduces pressure in the surrounding space This so-called flat module configuration allows to greatly reduce the flow resistance of eluent in comparison with the conventional capillary tube degassing unit, thereby enabling gases dissolved in the flowing eluent to go out efficiently from the walls of the flat hollow enclosure to the vacuum chamber with pressure reduced. Therefore, A time required for the eluent to pass through the degassing unit, that is, a time required for the eluent to be replaced is reduced, making it possible to make highly efficient chromatographic analyses.

(2) Also characterized is to form the aforementioned internal space of the flat hollow enclosure by closely fixing a spacer alongside the fringes between the two rectangular degassing film sheets constructing the flat hollow enclosure.

This construction allows to unitize the flat hollow enclosure, making it easy and simple to replace and maintain the degassing module.

(3) Characterized is to form the aforementioned internal space of the hollow enclosure by fitting each of the two degassing film sheets to one of the aforementioned sheet plate with holes, by placing the spacer alongside the fringes of the two film sheets between them, and by closely fixing them together with a pair of the aforementioned holding frames.

This construction allows to unitize the sheet plates with holes as well, making it easy and simple to replace and maintain the degassing module.

(4) Characterized is to provide a temperature control device with the aforementioned degassing unit, which allows to control the temperature of the working environment of the degassing unit independently from its external atmosphere.

This construction allows to heat or cool the degassing unit to set optimum conditions regardless of an ambient atmosphere, thereby allowing to perform accurate chromatographic analyses.

(5) Employed as a material for the degassing film sheets is an anti-organic solvent material of thin film. By employing a polytetra-fluoro-ethylene (PTFE) sheet, for example, as an anti-organic solvent material of thin film, it avoids analysis errors caused by impurities. It also permits the life of the degassing module to be longer.

(6) Employed for the aforementioned sheet plate with holes is an anti-organic solvent material made of small wires in mesh. By using a material of, for example, stainless steel wires in mesh as the anti-organic solvent material, it can afford a large opening rate in the sheet, thereby passing quickly gaseous compounds coming out of the degassing film sheet and avoiding a condensation of dew.

This invention also allows to use any material which has the same performance and function as those required for the above mentioned degassing film sheet and the sheet plate with holes.

Furthermore, it is needless to state that this invention is not limited to the compositions and configurations described in the above clauses from (1) to (6), and allows to alter them unless it deviates from the concept of this invention stated throughout the descriptions of this file.

BRIEF DESCRIPTION OF THE DRAWINGS

FIGS. 11(a) an 11(b) illustrate a conventional degassing unit.

DETAILED DESCRIPTION OF PREFERRED EMBODIMENTS

Embodiments of the present invention are now described hereinafter with reference to the drawings.

Figure 1:
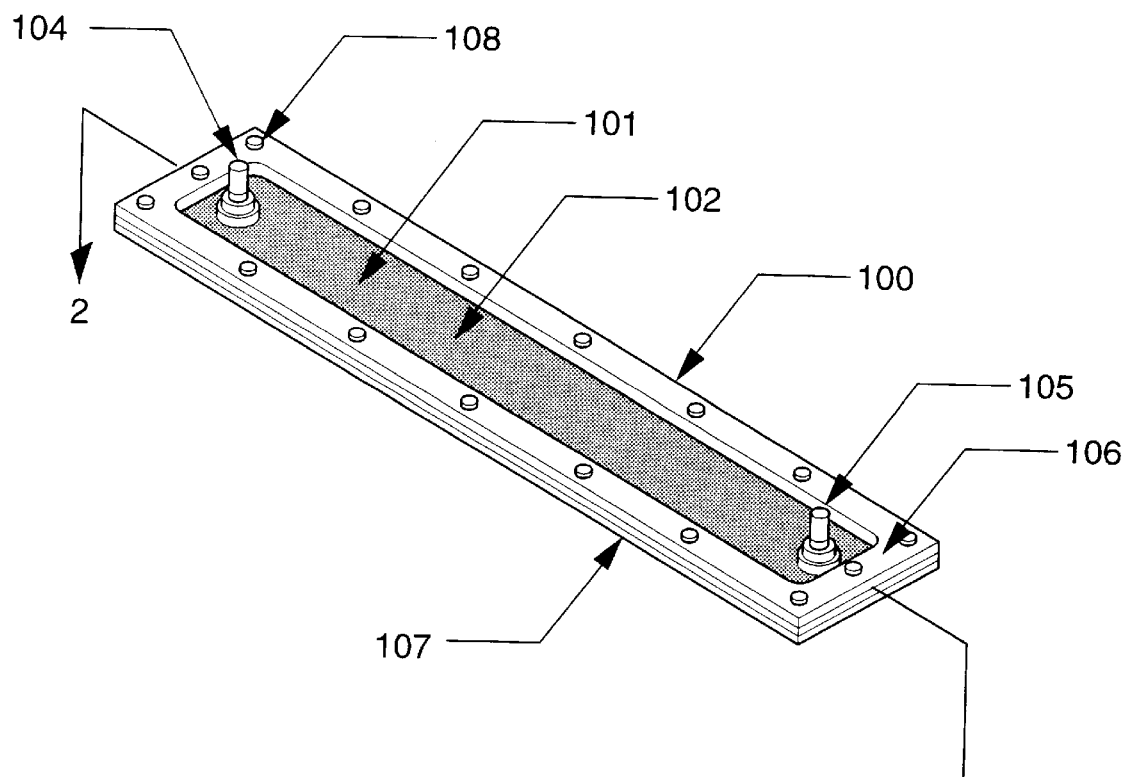
FIG. 1 is a perspective view showing a first embodiment of the degassing unit of this invention for HPLC.
Figure 2:
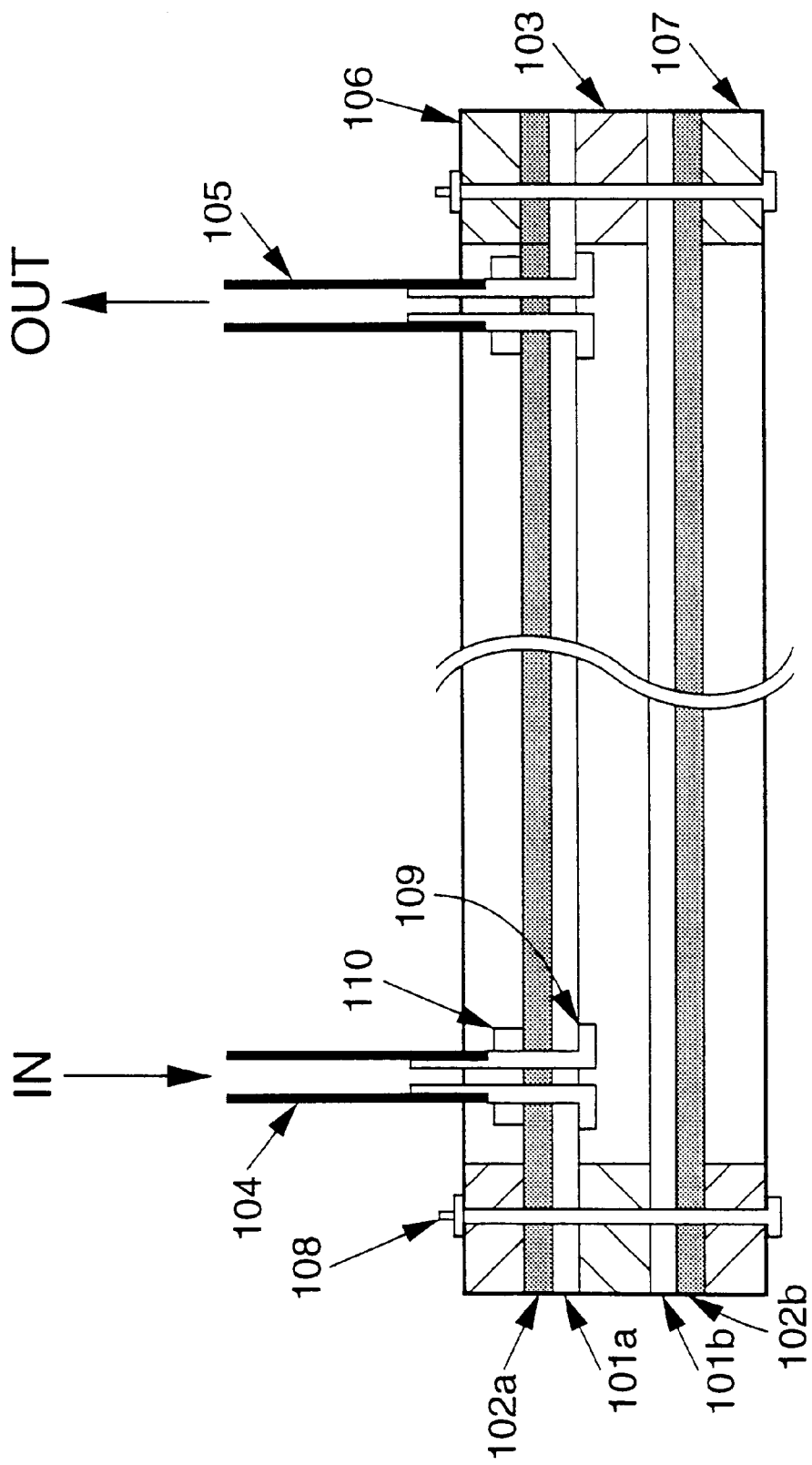
FIG. 2 is a cross-sectional view taken along the line 2—2 in FIG. 1.

FIG. 1 is a perspective view to show a first embodiment of the degassing module for HPLC according to this invention. FIG. 2 is a view in cross-section taken along the line 2—2 of FIG. 1.

In FIG. 1, the degassing module for the degassing unit of this invention is shown by 100. It is accommodated in a vacuum chamber (hermetically sealed case) with the same function as the one described in FIGS. 11(a) and 11(b), which is omitted in FIG. 1.

Figure 3:
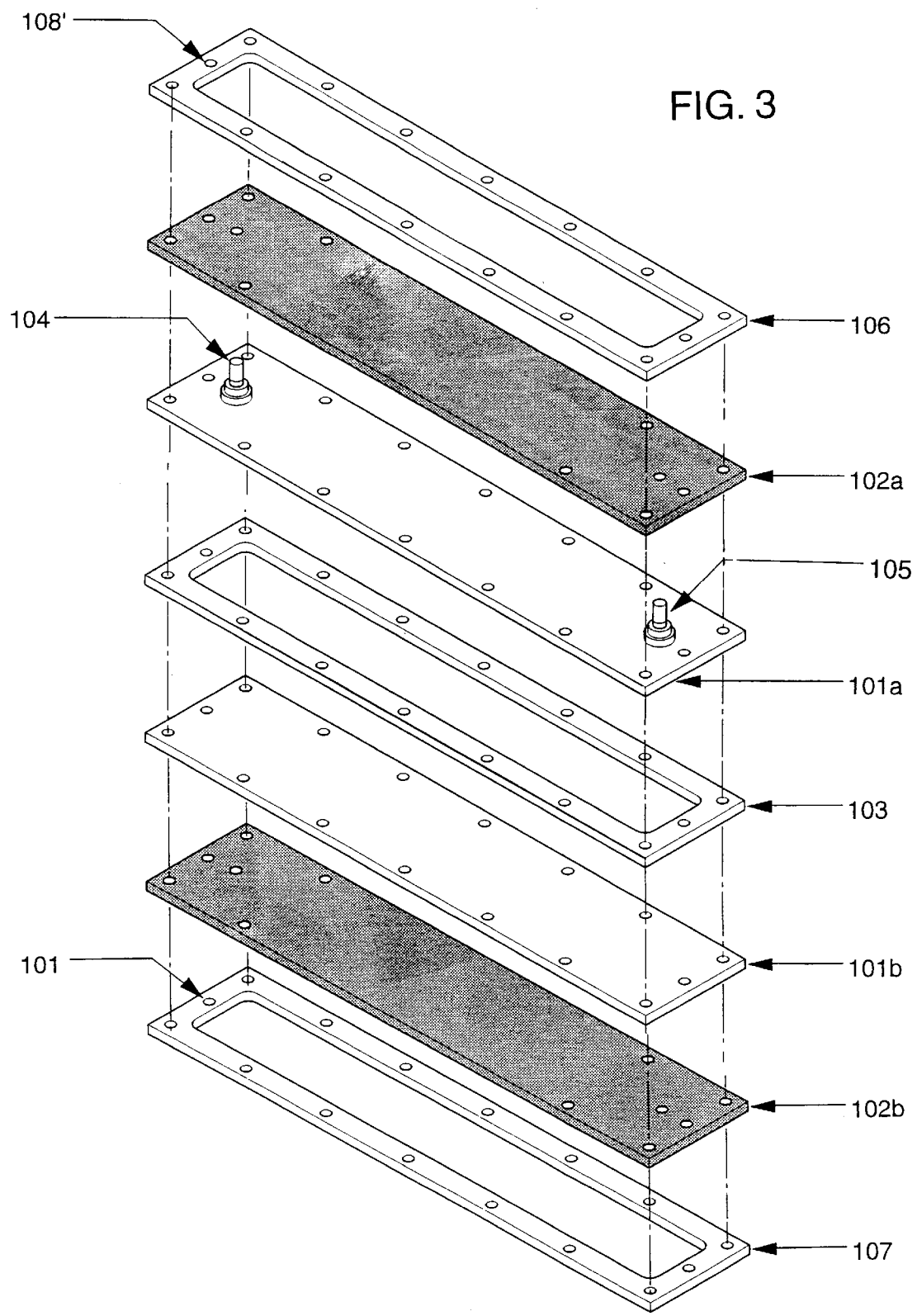
FIG. 3 is an exploded view in perspective, illustrating in detail the assembly and composition of the degassing module related to the first embodiment of this invention.

FIG. 3 is an enlarged perspective view to indicate a detailed assembling composition of the degassing module.

In FIGS. 1, 2 and 3, this degassing module 100 is composed of the two PTFE film sheets 101a and 101b with a spacer 103 placed in between on their fringes as well as the two stainless steel mesh sheets 102a and 102b put on to the PTFE film sheets 101a and 101b, respectively. They are held by upper and lower holding frames 106 and 107, and are fastened in one unit by fixing bolts 108.

By means of this fixing, the fringes of the two PTFE sheets are closely contacted and form the hollow enclosure to create the internal space between them. The hollow enclosure is provided on one side of the PTFE sheet (101a) with an inlet 104 to feed the eluent in to and an outlet to feed it out from the internal space. The inlet 104 is equipped on one short side of the rectangular PTFE sheet 101a and the outlet 105 on its other short side, respectively, thereby securing an eluent flowing pass to contribute to the degassing of the eluent.

The inlet 104 and the outlet 105 are composed each of a connector 109 and its fastening part 110 both of which are fitted to an opening provided by getting through the PTFE sheet 101a and the stainless steel mesh sheet 102a. The connector 109 is connected on its outside with a pipe fed to the exterior. The connector is preferably made of PTFE resin, but any material may be used if it is of organic solvent proof.

The PTFE sheet is supported by the mesh sheet of high precision stainless steel fibers of small diameter, and therefore, it is possible to use even a thin and mechanically weak film of the PTFE sheet. As the degassing effect is in inverse proportion to the thickness of the film, the degassing efficiency can be greatly increased by making the film thin with the stainless steel mesh sheet supported.

The eluent is fed in from the inlet 104 and transfers through the narrow internal space formed by the two PTFE sheets 101a and 101b. The eluent transfer is made by the pumping operation of a pump connected via the pipe to the outlet 105.

While the eluent transfers from the inlet 104 to the outlet 105, it spreads in the internal space formed by the PTFE sheets 101a and 101b and dissolved gaseous compounds are transmitted by reducing the pressure in the vacuum chamber by means of a vacuum pump (which is not shown in the figure) through the walls of the two PTFE sheets 101a and 101b, thereby dispersing into the vacuum chamber.

While the gases dissolved in the eluent come out across the PTFE sheets 101a and 101b and disperse into the chamber, a small amount of the eluent also gets out to the chamber and emerges on the surfaces of the PTFE sheets. Some of the eluent are vaporized in the chamber and some liquefied on the surfaces of the sheets.

Figure 4:
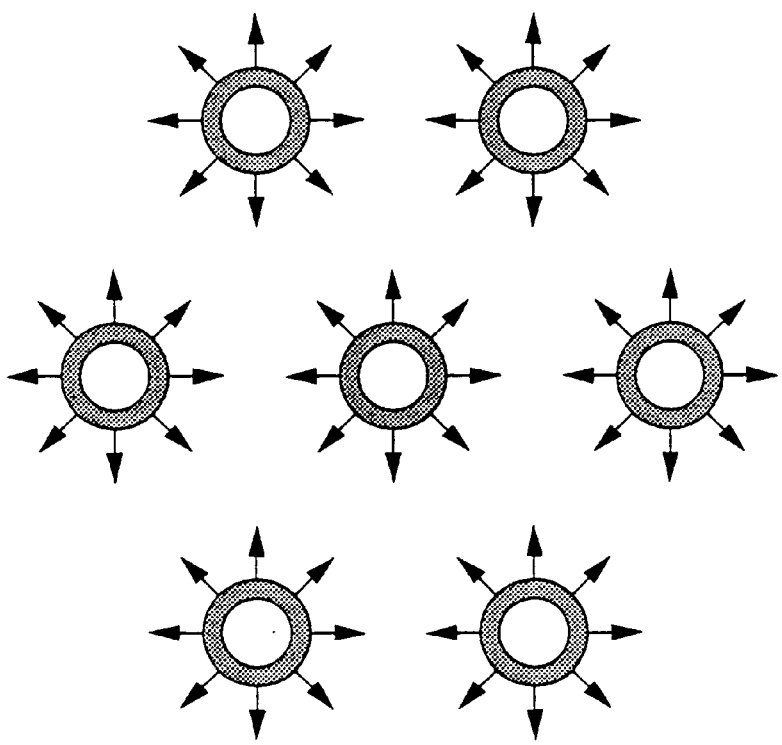
FIGS. 4(a) and 4(b) illustrate and show how liquid compounds are dispersed from the degassing modules of the conventional type and of the type in this embodiment of this invention.
Figure 4:
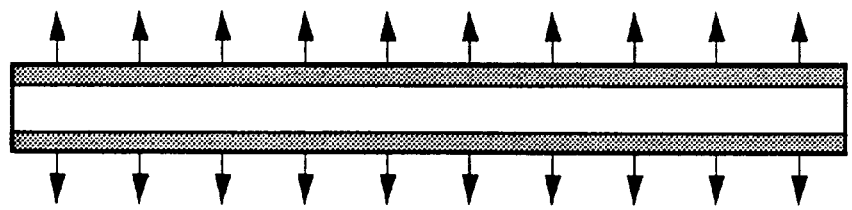

FIGS. 4(a) and 4(b) illustrate to explain how liquefied one is dispersed in the degassing modules, with FIG. 4(a) showing for a conventional capillary tube degassing module and FIG. 4(b) showing the flat degassing module of this invention.

In the case of the capillary degassing module shown by FIG. 4(a), tubes in which the eluent flows are surrounded by the same tubes each other, and therefore, the vaporizing efficiency of the eluent getting out of the capillary walls is low.

On the other hand, in the case of the flat degassing module shown by FIG. 4(b), that of the eluent out of the sheet walls is high as there is sufficient space secured on the upper and lower surfaces of the PTFE sheets. Furthermore, in this embodiment, as the stainless steel mesh sheet firmly attaches to each of the PTFE sheet surfaces, the eluent liquefied on the sheet surface is immediately absorbed into the small holes of the mesh sheet due to the capillary action, disperses into the wide mesh surfaces, and quickly vaporizes. Because of this, the small amount of the eluent emerging out onto the sheet surface does not condense into dewdrops there. However, when the degassing module is at around a room temperature, the surface temperature of the stainless steel mesh sheet is decreased quickly because of the quick vaporization, thereby making the degassing efficiency decreased.

Figure 5:
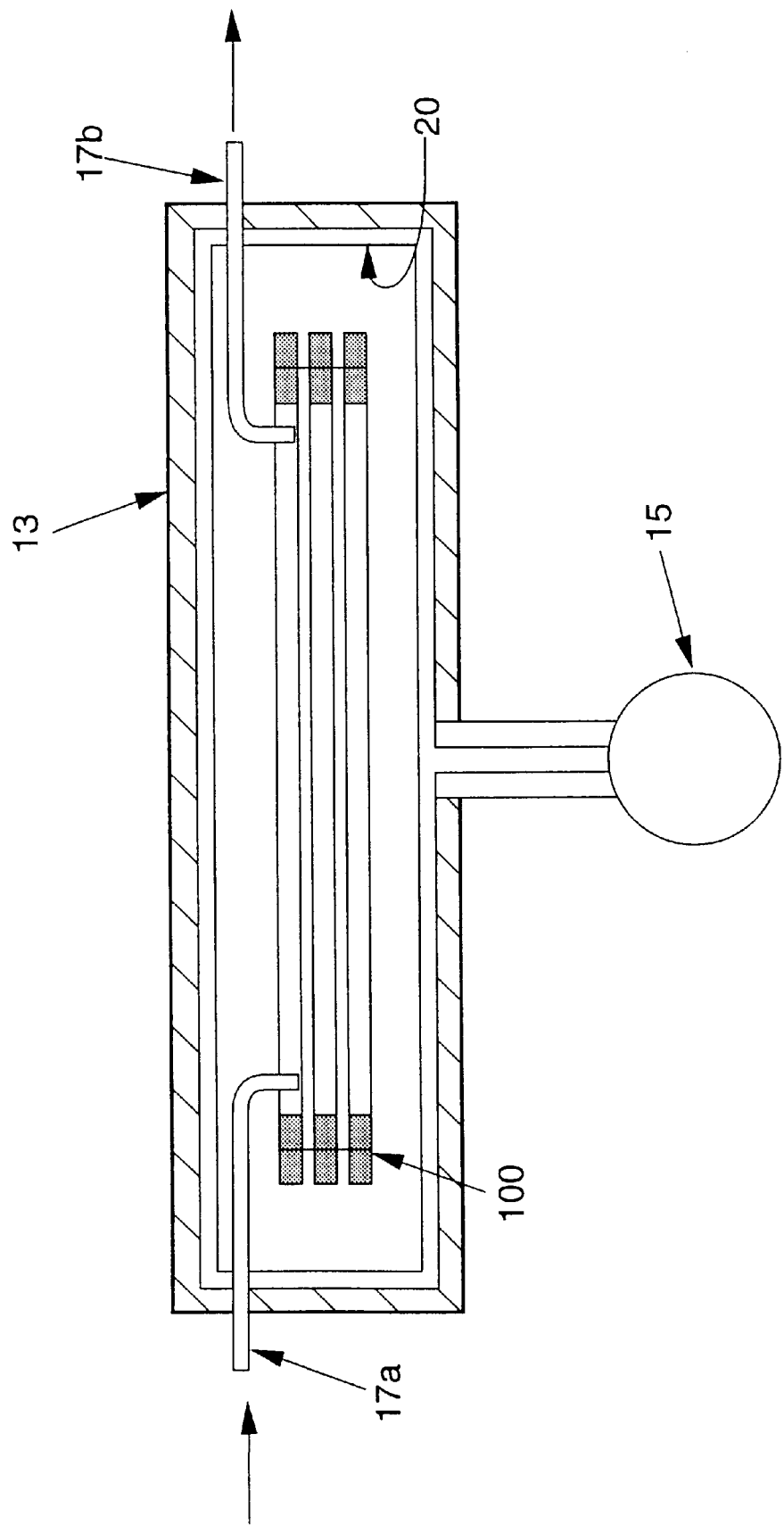
FIG. 5 is a diagrammatic cross-sectional view showing the overall composition of the degassing unit in the first embodiment of this invention.

FIG. 5 is a schematic cross section of the first embodiment for the degassing unit of this invention. With the same identification numbers as those in FIGS. 11(a) and 11(b) put for the same functions, 20 shows a heater for a temperature control unit and 100 shows the degassing module. As mentioned, a small amount of the liquid compounds getting out of the PTFE sheets is vaporized in the stainless steel mesh sheet, which causes the temperature of the degassing module to be decreased, thereby making the degassing efficiency deteriorated. The efficiency is more deteriorated especially in winter when room temperature becomes low.

In this embodiment, the vacuum chamber is so composed as to equip the temperature control unit with a heater 20, thereby allowing the temperature of the degassing module 100 to be adjusted. The inside temperature of the vacuum chamber is adequately controlled by this heater, which prevents the temperature decrease of the degassing module, thus the degassing efficiency deterioration is avoidable. According to this embodiment, the degassing unit which is capable of degassing at the high fluid replacement efficiency with the small volume can be provided.

Figure 6:
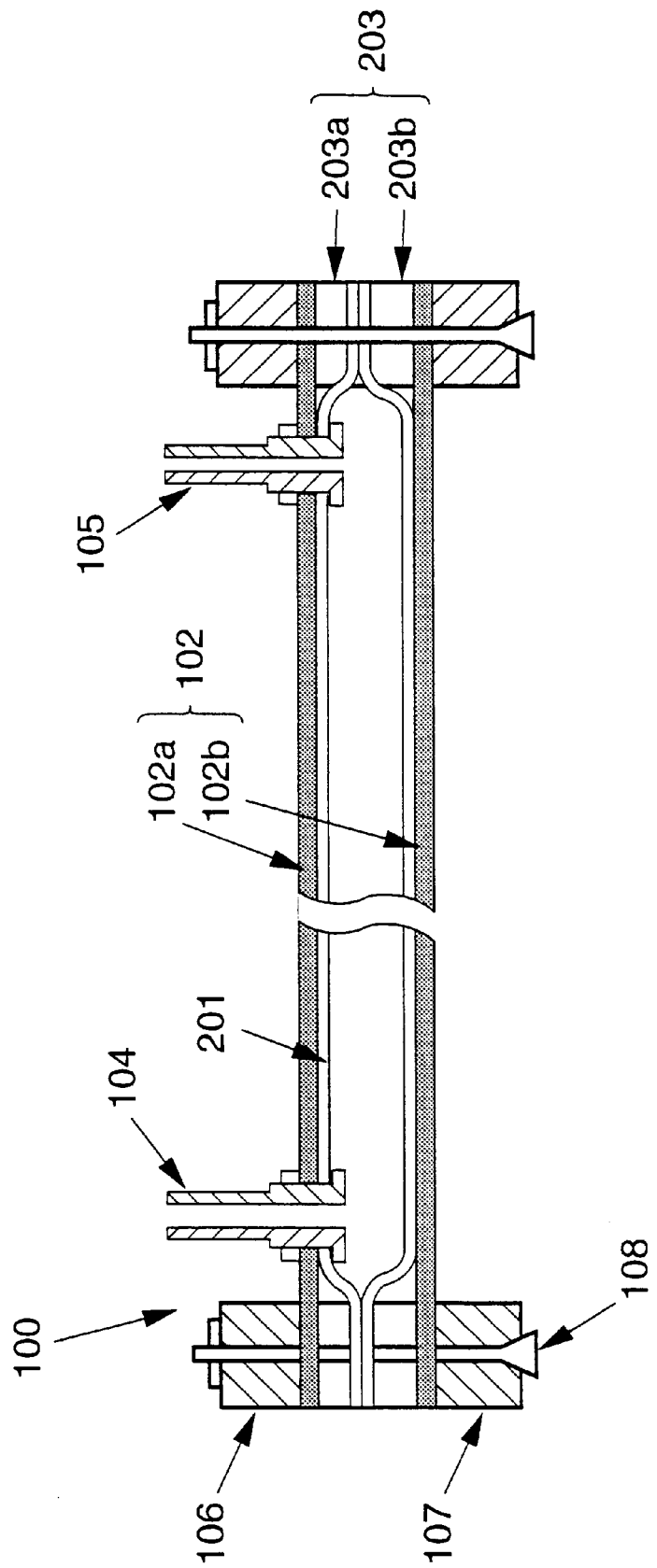
FIG. 6 is a cross-sectional view showing a second embodiment of the degassing unit of this invention for HPLC.

FIG. 6 shows a view in cross section of a degassing unit which is a second embodiment of this invention for HPLC.

Figure 7:
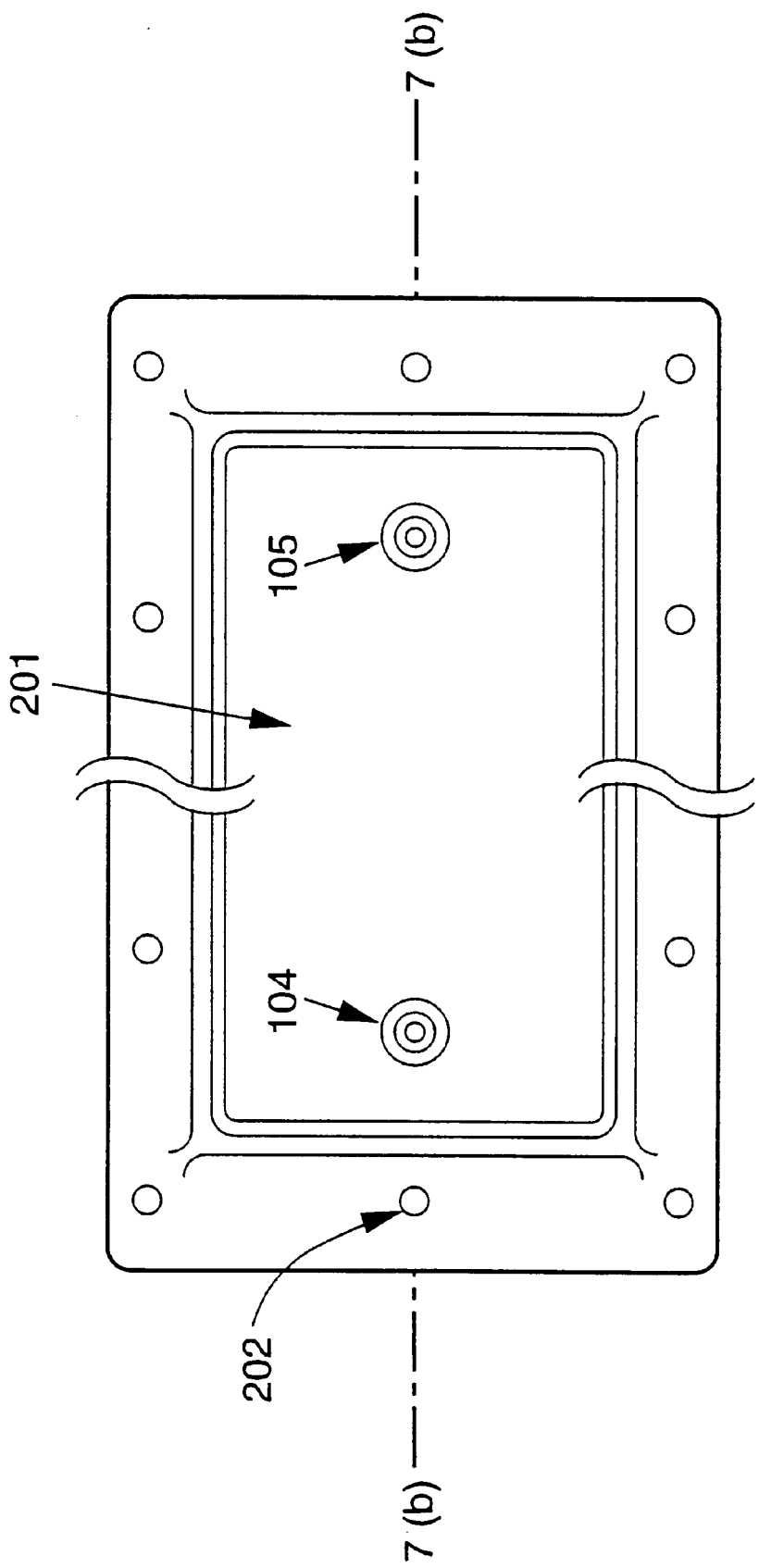
FIGS. 7(a), (b), and (c) illustrate in plan and cross-sectional views the degassing module shown in FIG. 6.
Figure 7:
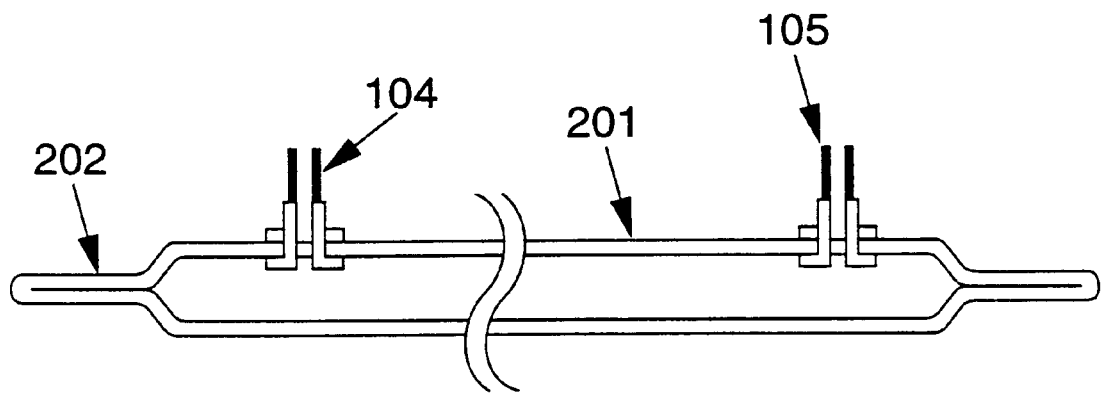
Figure 7:
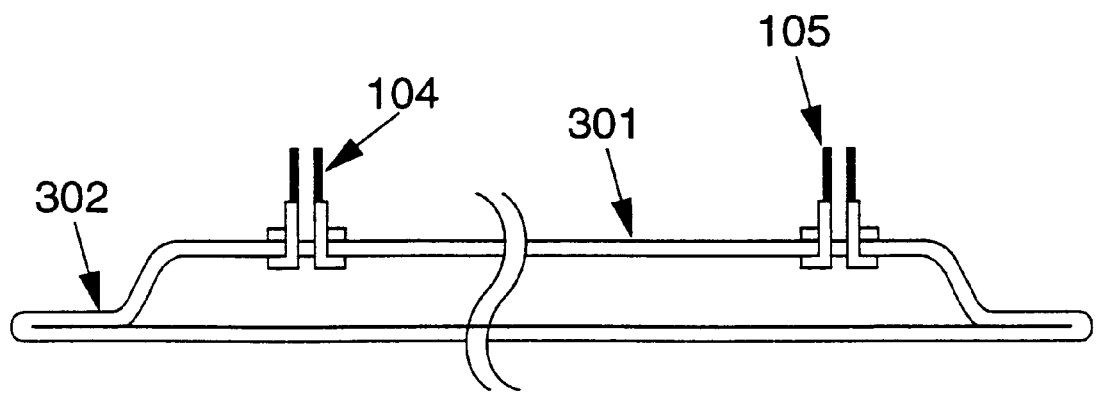

FIG. 7(a) relates to FIG. 6, and shows a top view of FIG. 6; FIG. 7(b) is a cross sectional view taken along the line of FIG. 7(b)—FIG. 7(b) and shows only the PTFE sheets, and FIG. 7(c) is a cross sectional view taken along the same longitudinal line of FIG. 7(b)—FIG. 7(b) but showing another alternate composition of the PTFE sheets.

In this modification or second embodiment as best shown in FIG. 6 and FIGS. 7(a), (b) and (c), the degassing room formed by the PTFE sheets is composed of an originally hollow, bag-shaped PTFE sheet 201 or 301.

As shown in FIG. 6 in which such hollow, bag-shaped PTFE sheets are employed as in FIG. 7(b), spacers 203 are placed on the upper and lower fringes of the bag-shaped sheets and between the upper and lower holding frames 106 and 107. 202 is a hole to insert a fixing screw 108. In such a case that the degassing room is formed by using PTFE sheets of different sizes as shown in FIG. 7(c), only one spacer is used as in the first embodiment and it is placed between the one side of the PTFE sheet fringe and one of the holding frames. By this embodiment as well, the degassing unit which is capable of the high fluid replacement efficiency with the small volume can be provided.

Figure 8:
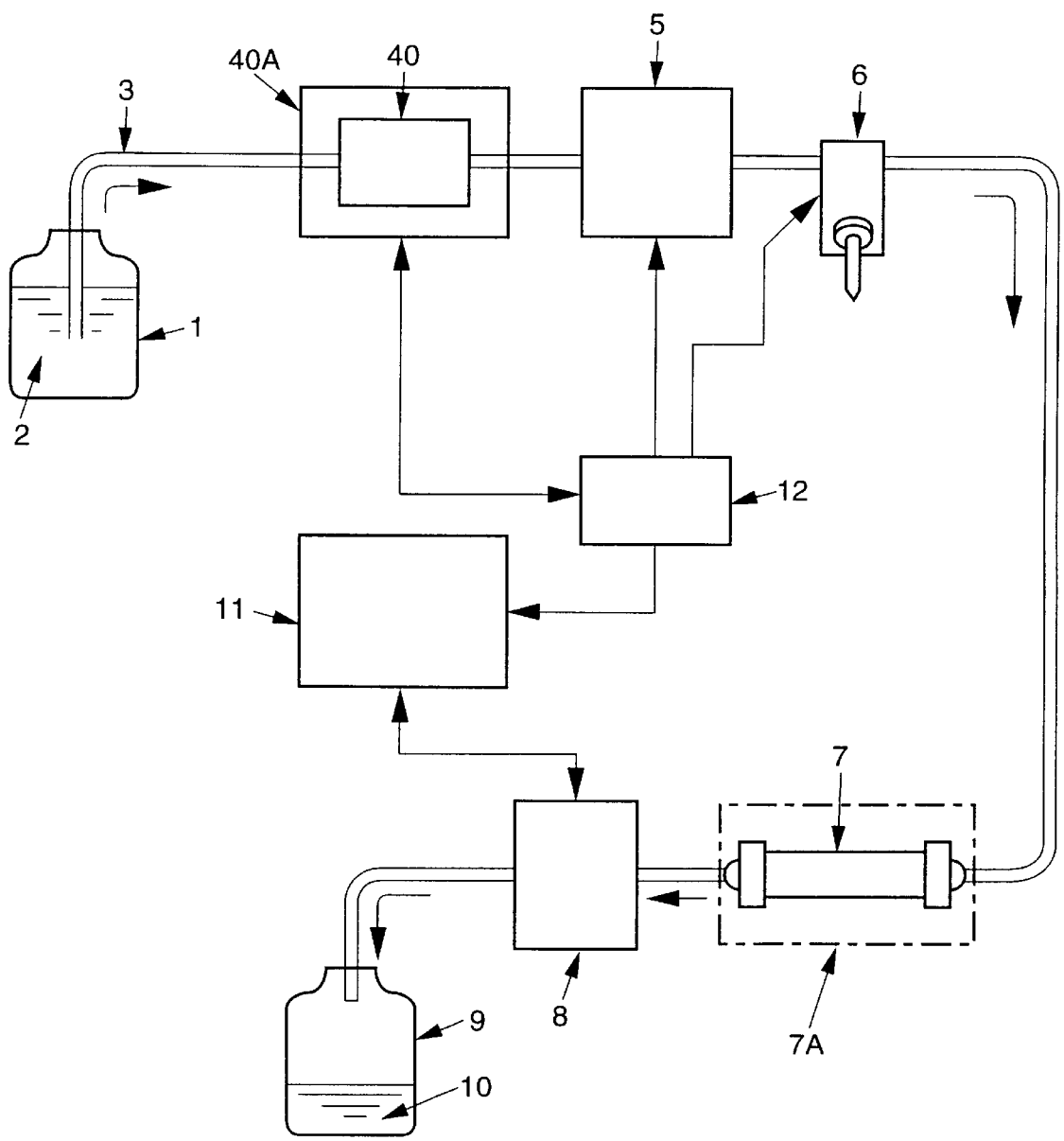
FIG. 8 is a block diagram illustrating a system configuration of HPLC according to this invention.
Figure 10:
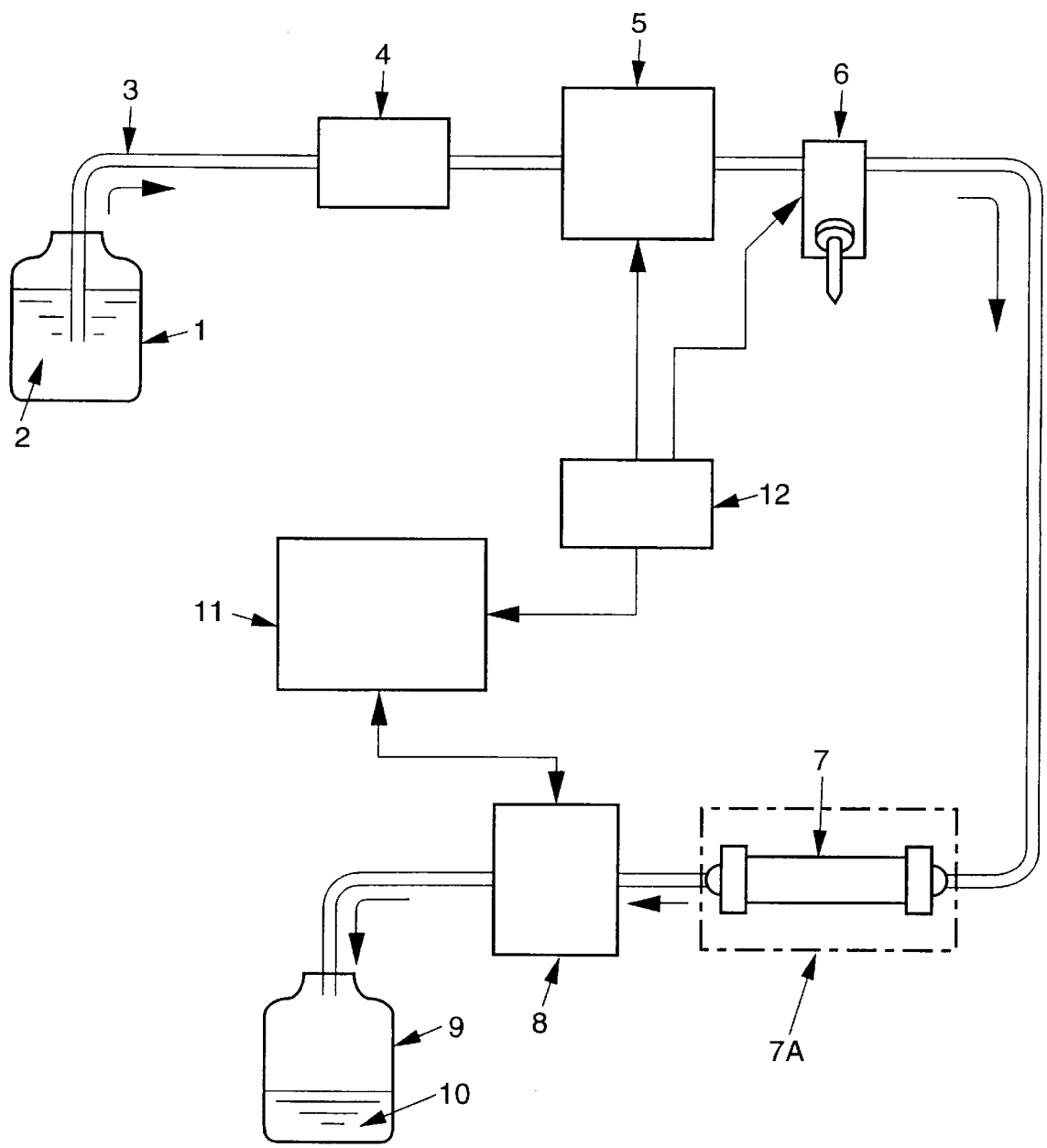
FIG. 10 is a block diagram to show a system configuration of HPLC.

FIG. 8 is a schematic diagram to explain a system configuration using this invention for HPLC. The same identification numbers are put on as those in FIG. 10 for the same functions, with 40 for the degassing unit of this invention and 40A for the temperature control unit.

In this FIG. 8, an eluent 2 in a first reservoir 1 is drawn up by a pump 5 through a pipe 3 and degassed by a degassing unit 40. It is then delivered through a sample injection valve (auto sampler) 6 and a column 7 to a detector unit 8. The eluent delivered from the detector unit 8 is thrown out to a second reservoir 10 as a waste eluent 9. The arrow marks show the direction of the eluent delivery. Data detected by a detector unit 8 are transferred to a data processing unit 11, in which they are processed in a visual form or a computer processable data form to provide and store. The degassing unit 40 is provided with a temperature control unit 40A to adequately control the temperature. The temperature control unit 40A is controlled by a system controller 12.

The column 7 is accommodated in an isothermal oven 7A to prevent the influence of external temperature. The pump 5 and the sample injection valve 6 are controlled by the system controller 12 as well.

The degassing unit 40 installed before the pump 5 is more compact in size and higher in efficiency than any conventional unit, insuring the stable delivery of the fluid and the accurate analysis by removing gases dissolved in the eluent which is drawn up from the first reservoir 1 by the pump 5.

In the degassing unit of this embodiment, the degassing module and the pipe are connected by a connector with an extremely small dead volume, thereby realizing to make the internal volume of the degassing module small to an extent of 1.6 ml required to degas at a flow rate of 0.2 ml/min. in semi-micro HPLC.

In terms of the efficiency to replace the eluent flown in the degassing module, the flat degassing module of this embodiment allows to improve the fluid replacement efficiency which used to be caused to deteriorate due to different flow rates of the conventional degassing module with a number of capillary tubes, for the channel to flow the eluent is single in the flat degassing module.

The volume required to replace the eluent in the flat degassing module is 9.8 ml in comparison with 65 ml by the conventional degassing module. Provided that an replacement capacity per unit time is 1 ml/min., the time to replace becomes theoretically 9.8 min. But, as the actual replacement capacity per unit time is 0.2 ml the time required to completely replace the internal eluent becomes 49 min. This is only one out of several compared with the aforementioned conventional technology.

Figure 9:
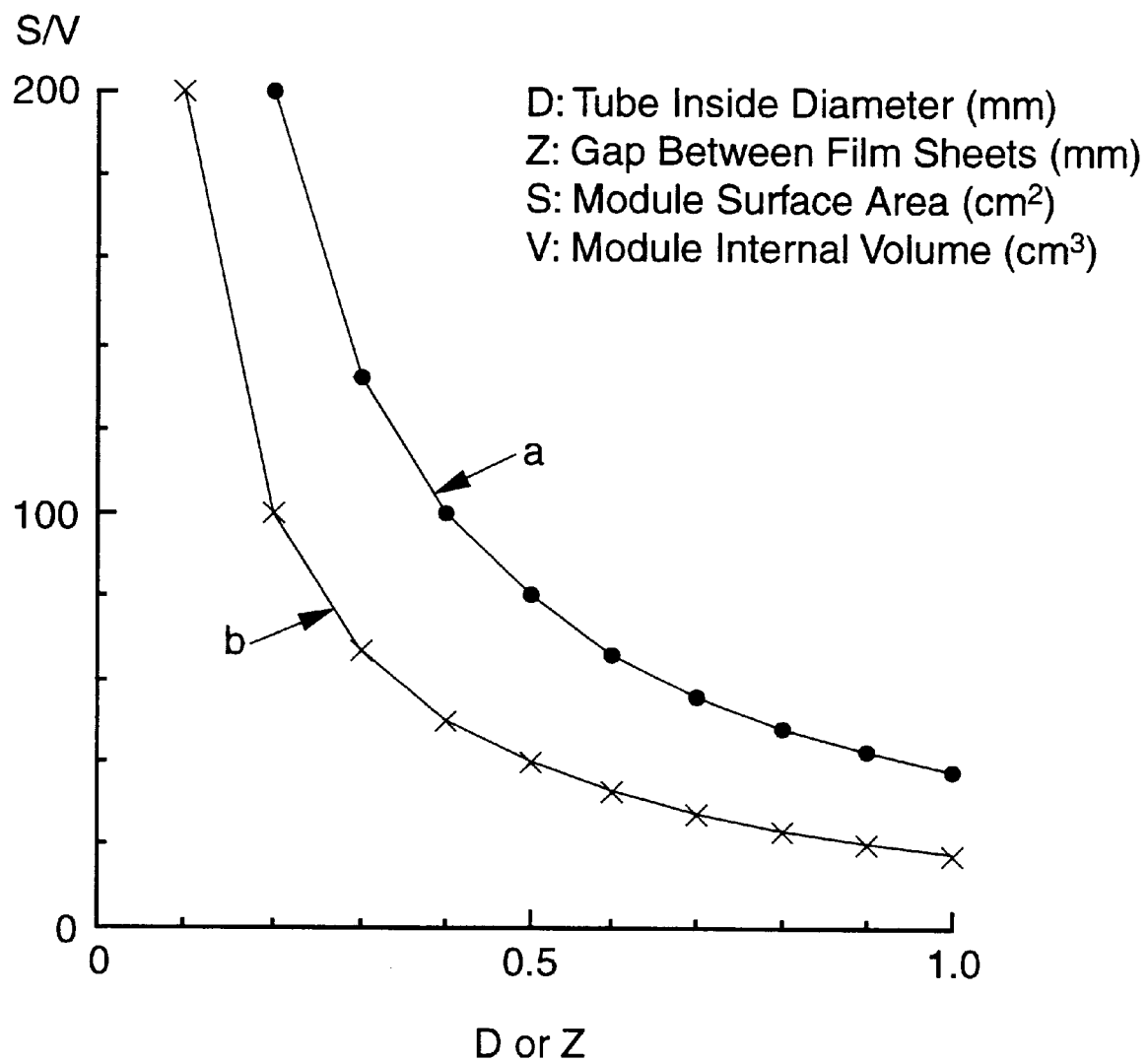
FIG. 9 is a graph showing a theoretical ratio of the surface area vs. the internal volume of degassing modules by the flat type of this invention and by the conventional capillary tube type.

FIG. 9 shows in graph a respective theoretical ratio of the surface area against the internal volume in the flat degassing module of this embodiment and in the conventional capillary tube degassing module.

In this graph, X-axis represents the inside diameter D (mm) of the capillary tube or the gap Z (mm) between the two degassing film sheets, and Y-axis represents the ratio S/V with the surface area S ($cm^2$) against the internal volume V ($cm^3$) of the degassing module.

The curve a represents the case of the capillary tubes, which S/V is obtained as below:

$$S/V = 2\pi(D/2) \times 10^{-2} / \pi(D/2)L \times 10^{-3} = 40/D$$

(Note) L means a length of the capillary tubes.

The curve b represents the case of the degassing film sheets, which S/V is obtained as below:

$$S/V = XY \times 10^{-2} \times 2 / XYZ \times 10^{-3} = 20/Z$$

(Note) X and Y mean a length and width of the degassing film sheets, respectively.

As shown in FIG. 9, in terms of the ratio S/V the capillary tube type is better in efficiency by twice than the flat sheet type, but it is not so much different. It can be said that the most important factor to influence the degassing efficiency lies in the time of transfer for the gases dissolved in the eluent to go dispersing into the walls of the tubes or the sheets. This time of transfer is in proportion to the thickness of the wall, and the thinner the wall the shorter the time of transfer, resulting in improving the degassing efficiency.

In the case of the capillary tube, its wall thickness is limited to 150 μm and if thinner than this it is mechanically difficult to process it and connect to the connector. Whereas, in the case of the flat film, there are no such difficulties and it is theoretically possible to compensate for the above-mentioned efficiency difference by employing the film sheet of less than 75 μm in thickness.

FIG. 9 also shows that the internal volume can be easily made smaller by using the film sheets than by the capillary tubes.

As described above, according to this embodiment the internal volume can be made small and at the same time the time required to degas the eluent can be shortened.

According to the invention, by performing the degassing with the single flat channel using such gas permeable resin films, such as PTFE sheets or other like material sheets, the degassing efficiency is improved and the volume of or size of the degassing module is rather small, thereby enabling a compact degassing unit to provide in a high speed, high precision HPLC system realizing the highly accurate liquid flow at high speed with very small quantity.

What is claimed:

1. In a degassing unit to be used for high performance liquid chromatography systems, which draws an eluent from a reservoir by a fluid delivery pump and which, removes gases dissolved in the eluent and delivers the gas removed eluent via a sample injection valve to a detection means including a separation column, the degassing unit being installed between the reservoir and the fluid delivery pump, and the degassing unit being characterized by having a degassing module comprising:

a flat hollow enclosure consisting of two degassable film sheets having fringes which are sealed hermetically to form an internal space, and having two independent openings at separate positions; one for an inlet to feed eluent in and the other for an outlet to feed said eluent out;

two sheet plates having a plurality of holes, of the same shape as that of said film sheets, each of which is closely fitted to either side of the film sheets to prevent the expansion of the internal spaces of said hollow enclosure;

a pair of holding frames about said fringes of said hollow enclosure and the fringes of the sheet plates and which permits exposure of said surface areas of said sheet plates; and a vacuum chamber for accommodating said degassing module and also providing a surrounding space around said degassing module, and, a vacuum pump which reduces pressure inside the said vacuum chamber.

2. The degassing unit of claim 1, wherein said internal space of said hollow enclosure is formed by a spacer disposed the fringes between said two degassing film sheets.

3. The degassing unit of claim 2, wherein an anti-organic solvent material of thin film is employed as a material for the degassing film sheets.

4. The degassing unit of claim 2, wherein an anti-organic solvent material made of small wires in mesh is employed as a material for said sheet plates.

5. The degassing unit of claim 1, wherein said internal space of said hollow enclosure is formed by fitting each of said two degassing film sheets to either one of said two sheet plates and placing a spacer about the fringes of the two film sheets and between said sheet plates, and securely fixing them together by said pair of holding frames.

6. The degassing unit of claim 5, wherein an anti-organic solvent material of thin film is employed as a material for the degassing film sheets.

7. The degassing unit of claim 5, wherein an anti-organic solvent material made of small wires in mesh is employed as a material for said sheet plates.

8. The degassing unit of anyone of claims 1, 2 and 5, further including a temperature control device to allow temperature in the working environment of said degassing unit to be controlled independently from its external atmosphere.

9. The degassing unit of claim 8, wherein an anti-organic solvent material of thin film is employed as a material for the degassing film sheets.

10. The degassing unit of claim 8, wherein an anti-organic solvent material made of small wires in mesh is employed as a material for said sheet plates.

11. The degassing unit of claim 1, wherein an anti-organic solvent material of thin film is employed as a material for the degassing film sheets.

12. The degassing unit of claim 11, wherein an anti-organic solvent material made of small wires in mesh is employed as a material for said sheet plates.

13. The degassing unit of claim 1, wherein said anti-organic solvent material made of small wires in mesh form is employed as a material for said sheet plates.

14. The degassing unit of claim 1, wherein said flat hollow enclosure is square in shape.

15. The degassing unit of claim 14, wherein said square is rectangular.

* * * * *

UNITED STATES PATENT AND TRADEMARK OFFICE
CERTIFICATE OF CORRECTION

PATENT NO. : 5,980,742
DATED : November 9, 1999
INVENTOR(S) : Toshinori SAITOH

It is certified that error appears in the above-identified patent and that said Letters Patent is hereby corrected as shown below:

Title page, insert item

[30]  Foreign Application Priority Data
      Nov. 11, 1997 [JP] Japan........9-308455

Signed and Sealed this

Third Day of April, 2001

Attest:

NICHOLAS P. GODICI

*Attesting Officer*    Acting Director of the United States Patent and Trademark Office